United States Patent [19]

Arold et al.

[11] Patent Number: 4,769,458

[45] Date of Patent: Sep. 6, 1988

[54] PROCESS FOR THE PREPARATION OF PHOSPHORIC ACID DERIVATIVES AND INTERMEDIATE PRODUCTS

[75] Inventors: Hermann Arold; Fritz Maurer, both of Wuppertal, Fed. Rep. of Germany

[73] Assignee: Bayer Aktiengesellschaft, Leverkusen, Fed. Rep. of Germany

[21] Appl. No.: 925,200

[22] Filed: Oct. 31, 1986

[30] Foreign Application Priority Data

Nov. 2, 1985 [DE] Fed. Rep. of Germany ....... 3538912

[51] Int. Cl.$^4$ ..................... C07F 9/65; C07D 239/36; C07D 239/52; C07D 239/54
[52] U.S. Cl. .................... 544/243; 544/298; 544/318; 544/319
[58] Field of Search ............... 544/243, 298, 318, 319

[56] References Cited

U.S. PATENT DOCUMENTS 4,665,175  5/1987  Maurer .............................. 544/243
4,686,290  8/1987  Maurer .............................. 544/243

OTHER PUBLICATIONS

Cooper et al., J. Chem. Soc., Perkin Trans I, pp. 2038–2045 (1976).
McOmie, "Protective Groups in Organic Chemistry", Plenum Press, N.Y. (1973), pp. 145–147, 171–177.
Greene, "Protective Groups in Organic Synthesis", John Wiley & Sons, N.Y. (1981), pp. 87–88, 101–107.
Hurst, Chemical Abstracts, vol. 100:34490h (1984).

*Primary Examiner*—Donald G. Daus
*Assistant Examiner*—Diana G. Rivers
*Attorney, Agent, or Firm*—Sprung Horn Kramer & Woods

[57] ABSTRACT

The process which comprises

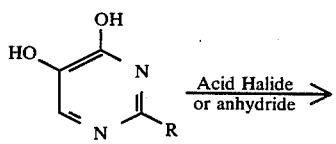

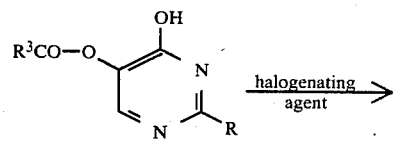

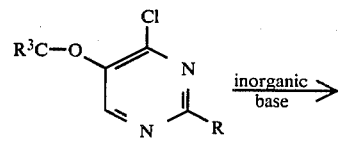

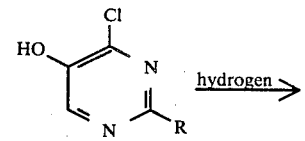

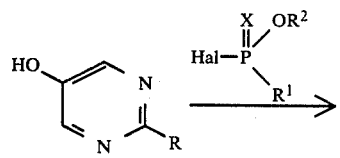

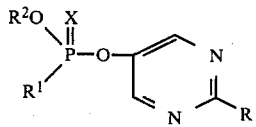

in which
R represents hydrogen, alkoxy, alkylamino or dialkylamino or represents optionally substituted radicals from the series comprising alkyl, cycloalkyl and aryl,
$R^1$ represents optionally substituted radicals from the series comprising alkyl, alkoxy, alkylthio, mono- or dialkylamino and phenyl,
$R^2$ represents optionally substituted alkyl,
$R^3$ represents alkyl, alkoxy or aryl,
X represents oxygen or sulphur, and
Y represents halogen or a grouping —OCOR$^3$.

The intermediates do not have to be isolated. Some are new compounds.

6 Claims, No Drawings

PROCESS FOR THE PREPARATION OF PHOSPHORIC ACID DERIVATIVES AND INTERMEDIATE PRODUCTS

The invention relates to a new process for the preparation of insecticidal pyrimidinylphosphoric acid derivatives, intermediate products which can be used for carrying out the process, and processes for the preparation of such intermediate products.

It is already known that certain pesticidal phosphoric acid pyrimidine esters are obtained when corresponding phosphoric acid ester-chlorides are reacted with 5-hydroxypyrimidines [compare U.S. Pat. No. 4,127,652 and DE-OS (German Published Specification No. 2,706,127].

However, this preparation method can be used only to a limited degree because of the absence of suitable starting compounds or because of unsatisfactory methods for their preparation. There is therefore a need for new intermediate products and a corresponding preparation process for phosphoric acid pyrimidine esters.

It has now been found that the compounds of the general formula (I)

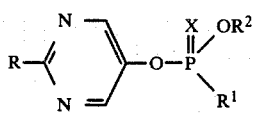

in which
R represents hydrogen, alkoxy, alkylamino or dialkylamino or represents optionally substituted radicals from the series comprising alkyl, cycloalkyl and aryl,
$R^1$ represents optionally substituted radicals from the series comprising alkyl, alkoxy, alkylthio, mono- or dialkylamino and phenyl,
$R^2$ represents optionally substituted alkyl and X represents oxygen or sulphur,
are obtained by a process in which
(a) compounds of the general formula (II)

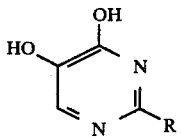

in which
R has the abovementioned meanings, are reacted with acylating agents of the formula (III)

$$R^3\text{—CO—Y} \qquad \text{(III)}$$

in which
$R^3$ represents alkyl, alkoxy or aryl and
Y represents halogen or a grouping —$OCOR^3$, if appropriate in the presence of acid acceptors and if appropriate in the presence of diluents at temperatures between 0° C. and 160° C. to give the compounds of the general formula (IV)

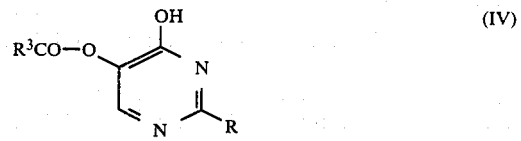

in which
R and $R^3$ have the abovementioned meanings, and, subsequently,
(b) the compounds of the general formula (IV), if appropriate after being isolated, are reacted with halogenating agents, if appropriate in the presence of N,N-disubstituted amides as catalysts and if appropriate in the presence of diluents, at temperatures between 10° C. and 120° C. to give the compounds of the general formula (V)

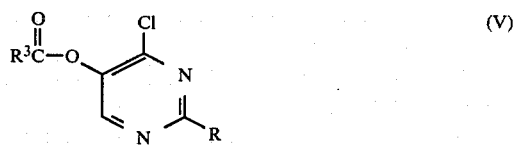

in which
R and $R^3$ have the abovementioned meanings, and, subsequently,
(c) the compounds of the general formula (V), if appropriate after being isolated, are reacted in the presence of inorganic bases at temperatures between 0° C. and 160° C. to give the salts of the compounds of the general formula (VI)

in which
R has the abovementioned meaning, with the bases used and, if appropriate, after liberation of the compounds of the general formula (VI) by acidification, subsequently
(d) the compounds of the general formula (VI) or their salts, if appropriate after being isolated, are reacted with hydrogen in the presence of hydrogenation catalysts, if appropriate in the presence of acid acceptors and in the presence of diluents, at temperatures between 20° C. and 150° C., to give the compounds of the general formula (VII)

in which
R has the abovementioned meaning, or their salts (with the bases used in Stage c)), and, if appropriate after liberation of the compounds of the general formula (VII) by acidification, subsequently
(e) the compounds of the general formula (VII) or their salts, if appropriate after being isolated, are reacted with compounds of the general formula (VIII)

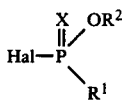 (VIII)

in which

Hal represents halogen and

X, $R^1$ and $R^2$ have the abovementioned meanings, if appropriate in the presence of an acid-binding agent, if appropriate in the presence of a bicyclic organic amine and if appropriate in the presence of a solvent, and the compounds of the general formula (I) are isolated.

It is possible to prepare the compounds of the formula (I) in a high purity and yield in a simple manner by this process. The process is very broadly applicable, in view of the nature of the desired substituents. Furthermore, the compounds to be employed as intermediate products are stable and can be stored and handled easily.

Preferred substituents and ranges of the radicals shown in the formulae mentioned above and below are illustrated below:

Alkoxy R represents straight-chain or branched alkoxy with preferably 1 to 12, in particular 1 to 6 and particularly preferably 1 to 4, carbon atoms. Examples which may be mentioned are methoxy, ethoxy, n-propoxy, i-propoxy, n-butoxy, i-butoxy, sec.-butoxy and tert.-butoxy.

Mono or di-alkylamino R represents an amino group with 1 or 2 alkyl groups, preferably 2 alkyl groups, which can be in each case straight-chain or branched and preferably contain 1 to 5, in particular 1 to 3, carbon atoms, methyl, ethyl and n- and i-propyl being mentioned. Examples which may be mentioned are dimethylamino, diethylamino, di-n-propylamino and di-i-propylamino.

Optionally substituted alkyl R represents straight-chain or branched alkyl with 1 to 20, preferably 1 to 12, in particular 1 to 6 and particularly preferably 1 to 4, carbon atoms. Examples which may be mentioned are optionally substituted methyl, ethyl, n-propyl, i-propyl, n-butyl, sec.-butyl, i-butyl, tert.-butyl, n-pentyl, i-pentyl and tert.-pentyl.

Optionally substituted cycloalkyl R represents cycloalkyl with preferably 3 to 8, in particular 3, 5 or 6, carbon atoms. Examples which may be mentioned are optionally substituted cyclopropyl, cyclobutyl, cyclopentyl, cyclohexyl and cycloheptyl.

Optionally substituted aryl R represents aryl with preferably 6 to 10 carbon atoms in the aryl part. Examples which may be mentioned are optionally substituted phenyl and naphthyl, in particular phenyl.

The substituted radicals mentioned in the definition of R can carry one or more, preferably 1 to 3 and in particular 1 or 2, identical or different substituents. Examples which may be mentioned of substituents for alkyl, cycloalkyl, and aryl are: alkoxy and alkylsulphonyl with 1 to 4 carbon atoms, such as methoxy, ethoxy, n-propoxy, i-propoxy, n-butoxy, i-butoxy, sec.-butoxy, tert.-butoxy, methylsulphonyl, ethylsulphonyl, n-propylsulphonyl, i-propylsulphonyl, n-butylsulphonyl, i-butylsulphonyl and tert.-butylsulphonyl.

Possible substituents on the aryl and substituents on the cycloalkyl are furthermore also $C_1$–$C_4$-alkyl, such as methyl, ethyl, n-propyl, i-propyl, n-butyl, i-butyl, sec.-butyl and tert.-butyl.

Preferably,

R represents hydrogen, or represents alkoxy with 1 to 12 carbon atoms, or represents mono- or dialkylamino with in each case 1 to 6 carbon atoms in the alkyl part, or represents alkyl which has 1 to 12 carbon atoms and is optionally substituted by $C_1$–$C_4$-alkoxy or $C_1$–$C_4$-alkylsulphonyl, or represents cycloalkyl which has 3 to 8 carbon atoms and is optionally substituted by $C_1$–$C_4$-alkyl, or represents aryl which has 6 to 10 carbon atoms and is optionally substituted by $C_1$–$C_4$-alkyl, $C_1$–$C_4$-alkoxy or $C_1$–$C_4$-alkylsulphonyl.

Particularly preferably,

R represents hydrogen, alkoxy with 1 to 6 carbon atoms or mono- or dialkylamino with in each case 1 to 4 carbon atoms in the alkyl part, or represents alkyl which has 1 to 6 carbon atoms and is optionally substituted by methoxy, ethoxy, methylsulphonyl or ethylsulphonyl, or represents cycloalkyl which has 3 to 6 carbon atoms and is optionally substituted by methyl or ethyl, or represents phenyl which is optionally substituted by methyl, ethyl, methoxy, ethoxy, methylsulphonyl or ethylsulphonyl.

Especially preferably,

R represents methyl, isopropyl or tert.-butyl, in particular isopropyl or tert.-butyl.

The optionally substituted alkyl groups $R^1$ and $R^2$ preferably contain 1 to 6, in particular 1 to 4 and particularly preferably 1 or 2, carbon atoms. Examples which may be mentioned are methyl, ethyl, n- and i-propyl and n-, i-, s- and t-butyl.

The alkyl groups of the optionally substituted alkyl- and dialkylamino groups $R^1$ preferably have the meaning given above as preferred for the alkyl groups $R^1$ and $R^2$. Examples which may be mentioned are methyl-, ethyl- and n- and i-propylamino and dimethyl-, diethyl- and methyl-ethyl-amino.

The alkoxy and alkylthio radicals $R^1$ preferably contain 1 to 6, in particular 1 to 4 and particularly preferably 1 or 2, carbon atoms. Examples which may be mentioned are methoxy, ethoxy and n- and i-propoxy and methylthio, ethylthio and n- and i-propylthio.

The optionally substituted radicals $R^1$ and $R^2$ can carry one or more, preferably 1 to 3 and in particular 1 or 2, identical or different substituents. Examples of substituents which may be mentioned are: alkyl (does not apply in the case in which $R^1$ or $R^2$ represents alkyl) with preferably 1 to 4, in particular 1 or 2, carbon atoms, such as methyl, ethyl, n- and i-propyl and n-, i-, s- and t-butyl; alkoxy with preferably 1 to 4, in particular 1 or 2, carbon atoms, such as methoxy, ethoxy, n- and i-propyloxy and n-, i-, s- and t-butyloxy; alkylthio with preferably 1 to 4, in particular 1 or 2, carbon atoms, such as methylthio, ethylthio, n- and i-propylthio and n-, i-, s- and t-butylthio; halogen, preferably fluorine, chlorine, bromine and iodine, in particular chlorine and bromine; and cyano and nitro.

$R^1$ preferably represents ethoxy or sec.-butoxy. $R^2$ preferably represents ethyl. X preferably represents sulphur.

Alkyl $R^3$ preferably represents $C_1$–$C_4$-alkyl, in particular $C_1$–$C_2$-alkyl, examples which may be mentioned being methyl, ethyl, n- and i-propyl and n-, i-, s- and t-butyl (particularly preferably methyl).

Alkoxy $R^3$ preferably represents $C_1$–$C_4$-alkoxy, in particular $C_1$–$C_2$-alkoxy, examples which may be mentioned being methoxy, ethoxy, n- and i-propoxy and n-, i-, s- and t-butoxy.

Aryl $R^3$ preferably represents aryl with 6 to 10 carbon atoms. Examples which may be mentioned are phenyl and naphthyl, in particular phenyl.

$R^3$ particularly preferably represents methyl.

Halogen Y and Hal denotes (unless indicated otherwise) fluorine, chlorine, bromine or iodine, preferably fluorine, chlorine or bromine, in particular chlorine.

In process step (a), the compounds of the general formula (II) are converted into the new compounds of the general formula (IV), if appropriate without being isolated. The compounds of the general formula (IV) and the process for their preparation according to process step (a) are part of the present invention.

It has thus been found that the new 4-hydroxypyrimidine derivatives of the general formula (IV)

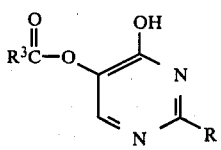
(IV)

in which

R and $R^3$ have the abovementioned meanings, are obtained when 4,5-dihydroxy-pyrimidines of the general formula (II)

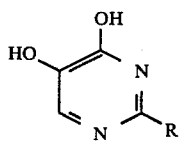
(II)

in which

R has the abovementioned meaning, are reacted with acylating agents of the formula (III)

$R^3$—CO—Y (III)

in which $R^3$ and Y have the abovementioned meanings, if appropriate in the presence of acid acceptors and if appropriate in the presence of diluents at temperatures between 0° C. and 160° C.

It is to be described as surprising that the new 4-hydroxy-pyrimidine derivatives of the formula (IV) are obtained in good yields and in a high purity by the process according to the invention or process step (a), since it was to be expected that both hydroxyl groupings would be acylated under the reaction conditions.

If 4,5-dihydroxy-2-methyl-pyrimidine is used as the starting substance and acetic anhydride is used as the acylating agent in the process according to the invention or process step (a), the reaction can be outlined by the following equation:

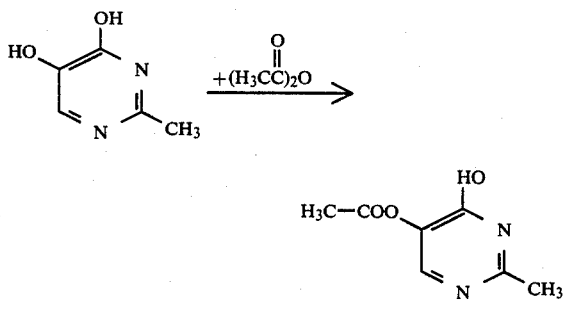

The following compounds may be mentioned as examples of the starting compounds of the general formula (II):

TABLE 1

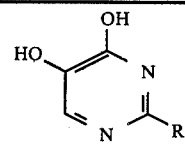
(II)

| R | R |
|---|---|
| H | OC$_2$H$_5$ |
| CH$_3$ | OC$_3$H$_7$—n |
| C$_2$H$_5$ | OC$_3$H$_7$—iso |
| C$_3$H$_7$—n | —CH$_2$OCH$_3$ |
| C$_3$H$_7$—iso | —CH$_2$CH$_2$OCH$_3$ |
| C$_4$H$_9$—n | —CH$_2$OC$_2$H$_5$ |
| C$_4$H$_9$—iso | —CH$_2$CH$_2$OC$_2$H$_5$ |
| C$_4$H$_9$—sec | —CH$_2$SO$_2$CH$_3$ |
| C$_4$H$_9$—tert | —CH$_2$CH$_2$SO$_2$CH$_3$ |
| C$_5$H$_{11}$—n | —CH$_2$CH$_2$SO$_2$C$_2$H$_5$ |
| C$_5$H$_{11}$—tert | —N(CH$_3$)$_2$ |
| OCH$_3$ | —N(C$_2$H$_5$)$_2$ |
| cyclopropyl-CH— | phenyl |
| cyclopentyl-H | p-tolyl (CH$_3$—C$_6$H$_4$—) |
| cyclohexyl-H | |

The compounds of the formula (II) to be employed according to the invention are known or can be prepared in a simple manner by known methods from 5-alkoxy-4-hydroxy-pyrimidines of the formula (IX)

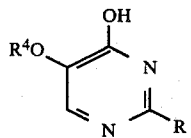
(IX)

in which

R has the abovementioned meanings and $R^4$ represents C$_1$-C$_4$-alkyl, and strong acids, such as, for example, hydrobromic acid or concentrated hydrochloric acid, at temperatures between 20° C. and 140° C. (compare J. Chem. Soc. 1963, 5590 and the preparation examples).

The compounds of the formula (IX) are known and/or can be prepared by known methods (compare DE-OS (German Published Specification) No. 2,639,256).

Examples which may be mentioned of the compounds of the formula (III) are acetic anhydride, acetyl fluoride, acetyl chloride, acetyl brqmide, benzoyl chloride, benzoic anhydride, methyl chloroformate, ethyl chloroformate, n-butyl chloroformate, dimethyl pyrocarbonate and diethyl pyrocarbonate. Acetic anhydride or acetyl chloride may be mentioned as particularly preferred.

The compounds of the formula (III) are generally known compounds of organic chemistry.

The process according to the invention for the preparation of the compounds of the general formula (IV) or process step (a) is preferably carried out in the presence of diluents. Preferred possible diluents are: aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone.

Bases which can be employed for the process according to the invention or process step (a) are virtually all the acid-binding agents which can usually be employed. These include, in particular: alkali metal and alkaline earth metal hydroxides and oxides, such as sodium and potassium hydroxides and, in particular, lithium hydroxide and calcium oxide or calcium hydroxide, alkali metal and alkaline earth metal carbonates, such as sodium, potassium and calcium carbonates, alkali metal alcoholates, such as sodium or potassium tert.-butylate, and furthermore aliphatic, aromatic or heterocyclic amines, such as triethylamine, dimethylaniline, dimethylbenzylamine, pyridine, diazabicyclooctane and diazabicycloundecene. If acid anhydrides are used as the acylating agent, the reaction is preferably carried out without an acid acceptor.

The reaction temperature can be varied within a substantial range. The reaction is in general carried out between 0° C. and 160° C., preferably at 20° C. to 140° C. The process according to the invention is in general carried out under normal pressure.

To carry out the process according to the invention or process step (a), the starting substances are usually employed in approximately equimolar amounts. An excess of one or the other of the reaction components provides no substantial advantages. The working up and the isolation which may be desired are effected by customary methods.

The following compounds may be listed as examples of the compounds of the formula (IV) obtainable according to the invention:

TABLE 2

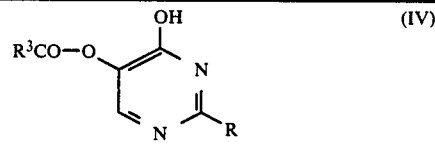

$R^3 = CH_3-, C_2H_5-, n-C_3H_7-,$  $, CH_3O-,$ $C_2H_5O-, n-C_4H_9O-$

| R | R |
|---|---|
| H | OC$_2$H$_5$ |
| CH$_3$ | OC$_3$H$_7$—n |

TABLE 2-continued

$R^3 = CH_3-, C_2H_5-, n-C_3H_7-,$  $, CH_3O-,$ $C_2H_5O-, n-C_4H_9O-$

| R | R |
|---|---|
| C$_2$H$_5$ | OC$_3$H$_7$—iso |
| C$_3$H$_7$—n | —CH$_2$OCH$_3$ |
| C$_3$H$_7$—iso | —CH$_2$CH$_2$OCH$_3$ |
| C$_4$H$_9$—n | —CH$_2$OC$_2$H$_5$ |
| C$_4$H$_9$—iso | —CH$_2$CH$_2$OC$_2$H$_5$ |
| C$_4$H$_9$—sec | —CH$_2$SO$_2$CH$_3$ |
| C$_4$H$_9$—tert | —CH$_2$CH$_2$SO$_2$CH$_3$ |
| C$_5$H$_{11}$—n | —CH$_2$CH$_2$SO$_2$C$_2$H$_5$ |
| C$_5$H$_{11}$—tert | —N(CH$_3$)$_2$ |
| OCH$_3$ | —N(C$_2$H$_5$)$_2$ |

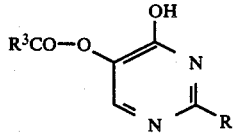

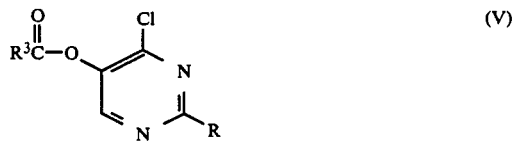

In process step (b), the compounds of the general formula (IV), if appropriate without being isolated, are converted into the new compounds of the general formula (V). The compounds of the general formula (V) and the process for their preparation according to process step (b) are part of the present invention.

It has thus been found that the new 4-chloropyrimidine derivatives of the general formula (V)

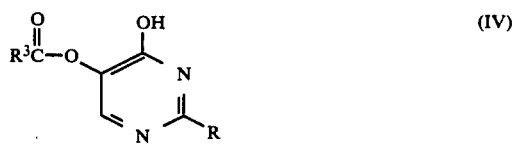

in which

R and R$^3$ have the abovementioned meanings, are obtained by a process in which 4-hydroxy-pyrimidine derivatives of the general formula (IV)

in which

R and $R^3$ have the abovementioned meanings, are reacted with halogenating agents, if appropriate in the presence of N,N-disubstituted amides as catalysts and if appropriate in the presence of diluents at temperatures between 10° C. and 120° C.

Surprisingly, the new 4-chloro-pyrimidine derivatives of the general formula (V) can be obtained in a simple manner according to the invention, although it had to be expected that side-chain reactions and/or cleavage reactions take place under the reaction conditions to form, for example, acid chlorides, or, for example, formylpyrimidines form when substituted amides are used ("Vilsmeyer reaction").

If, for example, 4-hydroxy-2-methyl-5-methylcarbonyloxy-pyrimidine is used as the starting substance and phosphorus oxychloride is used as the halogenating agent in the process according to the invention or process step (b), the reaction can be outlined by the following equation:

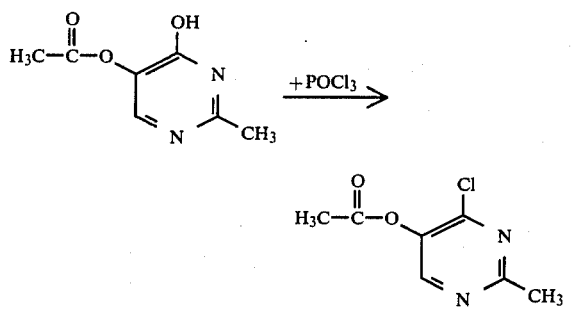

The process according to the invention for the preparation of the compounds of the general formula (V) or process step (b) is preferably carried out in the presence of diluents. Possible diluents are inert organic solvents, such as optionally halogenated aliphatic or aromatic hydrocarbons and polar solvents, for example amides. These include: benzene, toluene, xylene, chlorobenzene, o-dichlorobenzene, methylene chloride, ethylene chloride, chloroform, carbon tetrachloride and amides, such as, for example, dimethylformamide, N-methylformamide and N-methylpyrrolidone.

Halogenating agents which are used for the process according to the invention are the customary halogenating agents, preferably: phosphorus oxychloride, phosphorus trichloride, phosphorus pentachloride, oxalyl chloride, phosgene or thionyl chloride.

The process or process step (b) can be carried out in the presence of N,N-disubstituted amides as catalysts. Preferred possible N,N-disubstituted amides here are: dimethylformamide, N-methylformanilide, N-methylpyrrolidone and N-methylpiperidone.

The process according to the invention or process step (b) is in general carried out at temperatures between 10° C. and 120° C. The range between 20° C. and 100° C. is preferred. The reactions are in general carried out under normal pressure.

To carry out the process according to the invention or process step (b), 1 to 3 moles, preferably 1.1 to 2 moles, of halogenating agent and, if appropriate, 0.001 to 0.1 mole, preferably 0.005 to 0.05 mole, of N,N-disubstituted amide, as the catlayst, are employed per mole of the compund of the formula (IV). The working up and any desired isolation of the compounds of the general formula (V) are effected by customary methods.

The following compounds may be mentioned as examples of the compounds of the formula (V) obtainable according to the invention:

TABLE 3

(V)

[Structure of formula V shown]

$R^3 = CH_3-, C_2H_5-, n\text{-}C_3H_7-,$ [phenyl], $CH_3O-, C_2H_5O-, n\text{-}C_4H_9O-$

| R | R |
|---|---|
| H | $OC_2H_5$ |
| $CH_3$ | $OC_3H_7-n$ |
| $C_2H_5$ | $OC_3H_7-iso$ |
| $C_3H_7-n$ | $-CH_2OCH_3$ |
| $C_3H_7-iso$ | $-CH_2CH_2OCH_3$ |
| $C_4H_9-n$ | $-CH_2OC_2H_5$ |
| $C_4H_9-iso$ | $-CH_2CH_2OC_2H_5$ |
| $C_4H_9-sec$ | $-CH_2SO_2CH_3$ |
| $C_4H_9-tert$ | $-CH_2CH_2SO_2CH_3$ |
| $C_5H_{11}-n$ | $-CH_2CH_2SO_2C_2H_5$ |
| $C_5H_{11}-tert$ | $-N(CH_3)_2$ |
| $OCH_3$ | $-N(C_2H_5)_2$ |
| cyclopropyl | phenyl |
| cyclopentyl-H | $CH_3$-phenyl |
| cyclohexyl-H | |

In process step (c), the compounds of the general formula (V), if appropriate without being isolated, are converted into the compounds of the general formula (VI). The process for the preparation of the compounds of the formula (VI) is part of the present invention.

It has been found that the 4-chloro-5-hydroxypyrimidines of the general formula (VI)

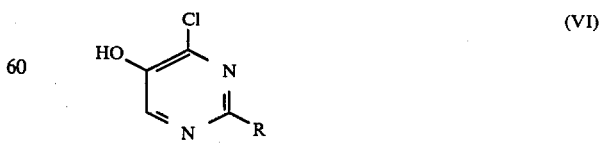

in which R has the abovementioned meanings, or their salts with inorganic bases are obtained by a process in which 4-chloro-pyrimidine derivatives of the general formula (V)

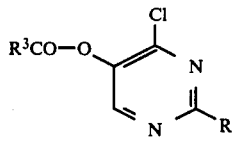

(V)

in which

R and R³ have the abovementioned meanings, are hydrolyzed, if appropriate in the presence of diluents, in the presence of inorganic bases at temperatures between 0° C. and 160° C. and, if appropriate, the compounds of the general formula (VI) are liberated by acidification.

Surprisingly, the 4-chloro-5-hydroxy-pyrimidines can be prepared in good yields and in a high purity. From knowledge of the prior art, halogen substitution (compare, for example, "The Chemistry of Heterocyclic Compounds", The Pyrimidines Volume/I, pages 148-149) such that the 4,5-dihydroxy-pyrimidine derivatives would form on basic hydrolysis would in fact have been expected.

If, for example, 4-chloro-2-methyl-5-methylcarbonyloxy-pyrimidine is used as the starting substance and the hydrolysis is carried out in the presence of sodium hydroxide solution, the reaction can be outlined by the following equation:

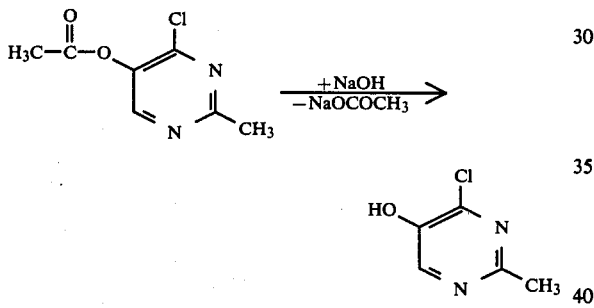

The process according to the invention for the preparation of the compounds of the formula (VI) or process step (c) is preferably carried out in the presence of diluents. The diluents which have already been mentioned in the description of process step (b) are preferably employed.

Inorganic bases which are preferably used for the process according to the invention are: alkali metal and alkaline earth metal hydroxides, such as, for example, sodium, potassium and calcium hydroxide, and alkali metal and alkaline earth metal carbonates, such as sodium, potassium and calcium carbonate.

The reaction temperature can be varied within a substantial range. The reaction is in general carried out between 0° C. and 160° C., preferably at 20° C. to 140° C. The process according to the invention is in general carried out under normal pressure.

To carry out the process according to the invention or process step (c), 1 to 5 moles, preferably 2 to 4.5 moles, of base are employed per mole of the compound of the formula (V). The working up and any desired isolation of the compounds of the formula (VI) are effected by customary methods. The compounds of the general formula (VI) are initially formed as salts of the bases used. They can be further reacted directly as salts. It is also possible to liberate the compounds of the general formula (VI) in the customary manner by acidification, for example with inorganic acids, such as hydrochloric acid or sulphuric acid.

The following compounds may be mentioned as examples of the compounds of the formula (VI) obtainable according to the invention:

TABLE 4

(VI)

| R | R |
|---|---|
| H | $OC_2H_5$ |
| $CH_3$ | $OC_3H_7$—n |
| $C_2H_5$ | $OC_3H_7$—iso |
| $C_3H_7$—n | —$CH_2OCH_3$ |
| $C_3H_7$—iso | —$CH_2CH_2OCH_3$ |
| $C_4H_9$—n | —$CH_2OC_2H_5$ |
| $C_4H_9$—iso | —$CH_2CH_2OC_2H_5$ |
| $C_4H_9$—sec | —$CH_2SO_2CH_3$ |
| $C_4H_9$—tert | —$CH_2CH_2SO_2CH_3$ |
| $C_5H_{11}$—n | —$CH_2CH_2SO_2C_2H_5$ |
| $C_5H_{11}$—tert | —$N(CH_3)_2$ |
| $OCH_3$ | —$N(C_2H_5)_2$ | and the salts, in particular the calcium, sodium and potassium salts, of these compounds.

In process stage (d), the compounds of the general formula (VII) or their salts (preferably calcium, sodium or potassium salts) are obtained from the compounds of the formula (VI) or salts thereof.

If, for example, 4-chloro-5-hydroxy-pyrimidine and Raney nickel, as the catalyst, are used for process stage (d), the reaction can be outlined by the folowing equation:

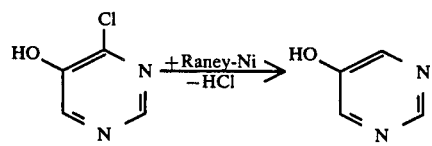

The solvents usually employed for hydrogenation reactions, such as water, lower aliphatic alcohols or carboxylic acids, such as methanol, ethanol or acetic acid, preferably water, are used for the preparation of the compounds of the general formula (VII) or their salts from the compounds of the general formula (VI) or salts thereof.

Acid acceptors which can be used are all the inorganic and organic bases which can usually be employed. These include, preferably, alkali metal carbonates, such as, for example, sodium and potassium carbonate; alkali metal hydroxides, such as, for example, sodium and potassium hydroxide, and lower tertiary alkylamines, cycloalkylamines and aralkylamines, such as, in particular, triethylamine.

Process stage (d) is carried out in the presence of a hydrogenation catalyst. Neutral metal catalysts, such as Raney nickel, Raney cobalt or palladium, if appropriate on customary support materials, such as, for example, active charcoal, are preferably employed.

The reaction temperatures can be varied within a substantial range. The reaction is in general carried out between 20° C. and 150° C., preferably between 20° C. and 100° C. and in particular between 40° C. and 80° C.

Process stage (d) is in general carried out under increased pressure, preferably between 5 and 100 bar and in particular between 7 and 60 bar.

To carry out process stage (d), between 1 and 5 moles, preferably between 2 and 3 moles, of acid acceptor and between 1 and 100 g, preferably between 5 and 50 g of catalyst are employed per mole of the compound of the formula (VI) or salts thereof.

The starting substances of the formula (VI) or salts thereof, the acid accepter, the catalyst and the diluent are mixed and hydrogen is forced in while the mixture is being heated up to the required temperature. Hydrogen is forced in at a constant temperature until a constant pressure indicates the end of the reaction. The compounds of the general formula (VII) can be liberated in the customary manner by acidification with inorganic acids (for example hydrochloric acid or sulphuric acid).

Examples which may be mentioned of the compounds of the general formula (VII) are:

TABLE 5

![structure VII: HO-pyrimidine-R]

(VII)

| R | R |
|---|---|
| H | OC$_2$H$_5$ |
| CH$_3$ | OC$_3$H$_7$—n |
| C$_2$H$_5$ | OC$_3$H$_7$—iso |
| C$_3$H$_7$—n | —CH$_2$OCH$_3$ |
| C$_3$H$_7$—iso | —CH$_2$CH$_2$OCH$_3$ |
| C$_4$H$_9$—n | —CH$_2$OC$_2$H$_5$ |
| C$_4$H$_9$—iso | —CH$_2$CH$_2$OC$_2$H$_5$ |
| C$_4$H$_9$—sec | —CH$_2$SO$_2$CH$_3$ |
| C$_4$H$_9$—tert | —CH$_2$CH$_2$SO$_2$CH$_3$ |
| C$_5$H$_{11}$—n | —CH$_2$CH$_2$SO$_2$C$_2$H$_5$ |
| C$_5$H$_{11}$—tert | —N(CH$_3$)$_2$ |
| OCH$_3$ | —N(C$_2$H$_5$)$_2$ | cyclopropyl—
phenyl—
cyclopentyl (H)—
p-tolyl (CH$_3$-C$_6$H$_4$—)
cyclohexyl (H)— and the salts, in particular the calcium, sodium and potassium salts, of these compounds.

The compounds of the formula (VII) or their salts are preferably prepared from the compounds of the formula (IV) without isolation of the particular intermediate products of the formulae (V) and (VI) and in accordance with the reaction conditions described under process steps (b), (c) and (d) (so-called "one-pot reaction").

This "one-pot reaction" is part of the present invention.

Surprisingly, the 5-hydroxy-pyrimidine derivatives of the general formula (VII) can be obtained in good yields and in a high purity by the "one-pot" process according to the invention, although it was to be expected that carrying out the above reaction steps in series without isolation and purification of the intermediate products would not lead to the desired products or, because of side reactions in individual stages, would lead to only low yields of impure compounds.

In process stage (e), the compounds of the general formula (I) are obtained from the compounds of the general formulae (VII) and (VIII). The compounds of the general formula (VII) can thereby also be employed in the form of their salts.

If, for example, 0-ethyl-0-isopropyl-thionophosphoric acid diester chloride and 5-hydroxy-2-phenyl-pyrimidine are used as starting substances in process stage (e), the corresponding reaction can be outlined by the following equation:

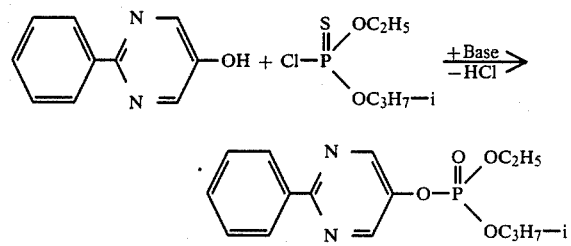

The starting substances of the general formula (VIII) to be employed in process stage (e) are known and can easily be prepared industrially by processes and methods which are known from the literature. Examples of these starting substances which may be mentioned specifically are: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diesterchloride and the corresponding thiono analogues, and furthermore O,S-dimethyl-, O,S-diethyl-, O,S-di-n-propyl-, O,S-di-iso-propyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl and O-sec.-butyl-S-ethylthiolphosphoric acid diester chloride and the corresponding thio analogues, and furthermore O-methyl-, O-ethyl-, O-n-propyl-, O-iso-propyl-, O-n-butyl-, O-iso-butyl- and O-sec.-butyl-methane- and -ethane-, -n-propane-, -iso-propane-, -n-butane-, -sec.-butane- and -phenyl-phosphonic acid ester chloride and the corresponding thio analogues, and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl-phosphoric acid monoester amide chloride and the corresponding thiono analogues. O-Ethyl-O-sec.-butyl-thionophosphoric acid diester chloride is particularly preferred.

Process stage (e) for the preparation of the compounds of the general formula (I) is preferably carried out by also using suitable solvents and diluents. Possible solvents and diluents are virtually all inert organic solvents. These include, in particular, aliphatic and aromatic, optionally chlorinated hydrocarbons, such as benzene, tolene, xylene, benzine, methylene chloride, chloroform, carbon tetrachloride and chlorobenzene, or ethers, such as diethyl ether, dibutyl ether or dioxane, and furthermore ketones, for example acetone, methyl ethyl ketone, methyl isopropyl ketone and methyl isobutyl ketone, and in addition nitriles, such as aceto- and propionitrile.

All the customary acid-binding agents can be used as acid acceptors. Acid acceptors which have proved particularly suitable are alkali metal carbonates and alcoholates, such as sodium and potassium carbonate and potassium tert.-butylate, and furthermore aliphatic, aromatic or heterocyclic amines, for example triethylamine, trimethylamine, dimethylaniline, dimethylbenzylamine and pyridine. If the compounds of the general formula (VII) are employed as salts, the addition of the acid acceptor can be dispensed with. Process stage (e) is preferably carried out in the presence of a bicyclic organic amine, such as quinuclidine and 1,4-diazabicyclo-(2,2,2)-octane (DABCO), preferably DABCO, as a catalyst. The bicyclic organic amine can at the same time also be used as the acid acceptor. In this case at least molar amounts of the bicyclic organic amine, in particular DABCO, are employed.

In a preferred embodiment, alkali metal carbonates, in particular $Na_2CO_3$ and/or $K_2CO_3$, are employed as acid acceptors and catalytic amounts of DABCO are employed as the catalyst.

Process stage (e) is in general carried out at temperatures between 0° C. and 120° C. The temperature range between 20° C. and 100° C. is preferred. The reactions are in general carried out under normal pressure.

To carry out process stage (e), 1.0 to 1.3 moles, preferably between 1.0 and 1.2 moles, of (thiono)phosphoric acid halide of the formula (VIII), and in the case where a bicyclic amine is used as the catalyst, 0.01 to 0.08 mole, preferably between 0.02 and 0.06 mole, of bicyclic organic amine (preferably DABCO) are employed per mole of the compound of the formula (VII) or of the salt. The reaction is in general carried out in a diluent and in the presence of an acid acceptor. The acid acceptor is added in amounts which are suitable for bonding the corresponding hydrogen halide. Preferably, 0.8 to 1.5, in particular 0.9 to 1.3 and particularly preferably 1.0 to 1.2, moles or equivalents of acid acceptor are employed per mole of the compound of the formula (VII). When the reaction has ended, the mixture is filtered and the solvent is distilled off in vacuo.

The compounds of the formula (I) are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. They are characterized by the refractive index.

The compounds of the general formula (I) obtainable according to the invention are distinguished by an outstanding insecticidal, acaricidal and nematicidal action. They have an action against plant pests, hygiene pests and pests of stored products and in the field of veterinary medicine. They have a good action both against sucking and against biting insects and mites, coupled with a low phytotoxicity.

For this reason, the compounds of the general formula (I) obtainable according to the invention can be successfully employed as agents for combating pests in plant protection and in the fields of hygiene, preservation of stored products and veterinary medicine.

The compounds of the formula (I) obtainable according to the invention can be applied in a known manner in the customary formulations (containing 0.5 to 95% of active compound), such as dusting powders, granules, emulsifiable concentrates, wettable powders or ultra-low-volume formulations, to the plants or spoil in the customary manner, if appropriate after dilution with water. About 0.1 to 2.5 kg of active compound are advantageously employed per hectare of area to be treated.

Many of the compounds obtainable according to the invention and their use are known and are described, for example, in DE-OS (German Published Specification) No. 2,643,262, DE-OS (German Published Specification) No. 2,714,771, U.S. Patent Specification No. 4,127,652, DE-OS (German Published Specification) No. 3,326,510, European Patent A 0,009,566, U.S. Patent Specification Nos. 4,325,948, 4,444,764, 4,429,125, 3,244,586 and DE-OS (German Published Specification) No. 3,317,824.

As already described above, it is possible to prepare the useful compounds of the general formula (I) in smooth reactions in a simple manner by the process according to the invention in process stages (a) to (e), outstanding overall yields being obtained. Process (a) to (e) according to the invention opens up, in a surprising manner by the particular combination of the process steps and by the use in some cases of new compounds thereby formed, a route which allows an inexpensive preparation of the compounds of the formula (I) which could not previously be achieved. Since the individual intermediate products are stable and above all, where they are isolated, can be stored for a prolonged period, the process according to the invention moreover permits exceptional flexibility in production, so that if demand foC the end products arises suddenly, production to meet demand is possible, which can be of very great importance, especially due to the wide seasonal variations caused by climate in the field of plant protection.

The processes (or process stages) and compounds according to the invention may be illustrated below by the following preparation examples:

Process for the preparation of the compounds of the general formula (IV) (process stage (a))

EXAMPLE (IV-1)

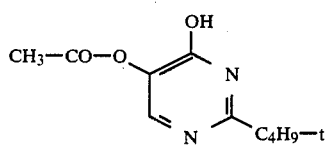

8.3 g (0.105 mole) of acetyl chloride are added to a mixture of 16.8 g (0.1 mole) of 2-tert.-butyl-4,5-dihydroxy-pyrimidine, 11.7 g (0.11 mole) of sodium carbonate and 100 ml of acetone, and the mixture is subsequently stirred for 3 hours, without heating. The inorganic salt is then filtered off with suction and rinsed with acetone and the filtrate is then evaporated in vacuo.

18.4 g (88% of theory) of 2-tert.-butyl-4-hydroxy-5-methylcarbonyloxy-pyrimidine are thus obtained in the form of pale yellow crystals of melting point 164° C.

EXAMPLE (IV-2)

A mixture of 84 g (0.5 mole) of 20tert. -butyl-4,5-dihydroxy-pyrimidine, 350 ml of toluene and 56.5 g (0.55 mole) of acetic anhydride is boiled under reflux for 6 hours. The volatile constituents are then completely distilled off in vacuo.

102 g (98% of theory) of 2-tert. -butyl-4-hydroxy-5-methylcarbonyloxy-primidine of melting point 163° C. are obtained.

The following compounds of the formula (IV) can be prepared analogoulsy to Example (IV-1) and (IV-2):

TABLE 6

| Example No. | R | $R^3$ | Acylating agent of the formula (III) |
|---|---|---|---|
| (IV-3) | C$_4$H$_9$—tert. | C$_4$H$_9$—tert. | tert.-C$_4$H$_9$COCl |
| (IV-4) | H | CH$_3$ | CH$_3$COCl |
| (IV-5) | ⌀(cyclohexyl/phenyl) | CH$_3$ | (CH$_3$CO)$_2$O |
| (IV-6) | cyclopropyl (H$_2$C-CH-CH$_2$) | CH$_3$ | CH$_3$COCl |
| (IV-7) | C$_4$H$_9$—tert. | phenyl | phenyl-COCl |
| (IV-8) | OCH$_3$ | CH$_3$ | CH$_3$COCl |
| (IV-9) | N(CH$_3$)$_3$ | CH$_3$ | CH$_3$COCl |

Process for the preparation of the compounds of the general formula (V) (process stage (b))

EXAMPLE (V-1)

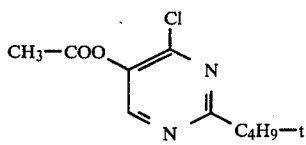

A mixture of 10.5 g (0/05 mole) of 2-tert. butyl-4-hydroxy-5-methylcarbonyloxy-pyrimidine and 20 ml of phosphoryl chloride is stirred at 60°–70° C. for ½ hour and then evaporated in vacuo. About 200 g of ice are added to the residue and the mixture is extracted twice with 25 ml of methylene chloride each time. The combined organic phases are dried over sodium sulphate, the solvent is then stripped off in vacuo and the residue is distilled in vacuo.

6.8 g (60% of theory) of 2-tert. -butyl-4-chloro-5-methylcarbonyloxy-pyrimidine are thus obtained as a colorless oil with a boiling point of 64° C./0.01 mm Hg.

The following compounds of the formula (V) can be prepared analogoulsy to Example (V-I):

TABLE 7

| Example No. | R | $R^3$ |
|---|---|---|
| (V-2) | C$_4$H$_9$—tert. | C$_4$H$_9$—tert. |
| (V-3) | H | CH$_3$ |
| (V-4) | phenyl | CH$_3$ |
| (V-5) | cyclopropyl (H$_2$C-CH-CH$_2$) | CH$_3$ |
| (V-6) | C$_4$H$_9$—tert. | phenyl |
| (V-7) | OCH$_3$ | CH$_3$ |
| (V-8) | N(CH$_3$)$_2$ | CH$_3$ |
| (V-9) | SCH$_3$ | CH$_3$ |
| (V-10) | C$_4$H$_9$—tert. | OCH$_3$ |

Process for the preparation of the compounds of the general formula (VI) (process stage (c))

EXAMPLE (VI-1)

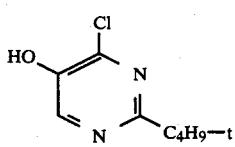

A mixture of 15 g of 45 per cent strength sodium hydroxide solution and 30 ml of water is added to a solution of 11.5 g (0.05 mole) of 2-tert. -bytyl-4-chloro-5methylcarbonyloxy-pyrimidine in 60 ml of toluene. The reaction mixture is stirred at 90° C. for 1 hour and the aqueous phase is separated off and freed from toluene residues in vacuo. The mixture is then adjusted to pH 4–5 by addition of concentrated hydrochloric acid, with cooling. The precipitated product is filtered off with suction and rinsed with water.

8.6 g (92% of theory) of 2-tert.-butyl-4-chloro-5-hydroxy-pyrimidine of melting point 112° C. are thus obtained.

EXAMPLE (VI-2)

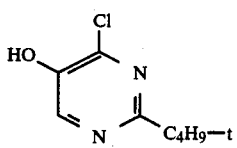

A solution of 2-tert.-butyl-4-chloro-5-methylcarbonyloxy-pyrimidine is prepared by warming a mixture of 10.5 g (0.05 mole) of 2-tert.-butyl-4-hydroxy-5-methylcarbonyloxy-pyrimidine, 50 ml of toluene, 0.1 ml of dimethylformamide and 30 ml of a 20 per cent strength phosgene solution in toluene at 60°–70°C. for 2 hours. This solution is added, without further purification, to a mixture of 17.5 g of 45 per cent strength sodium hydroxide solution and 30 ml of water and the mixture is then subsequently boiled under reflux for ½ hour. The aqueous phase is separated off, freed from residues of toluene in vacuo and then adjusted to pH 4–5 by addition of concentrated hydrochloric acid. The precipitated product is filtered off with suction, rinsed with water and dried in air.

8.3 g (89% of theory) of 2-tert.-butyl-4-chloro-5-hydroxy-pyrimidine are obtained in the form of beige crystals with a melting point of 112° C.

The following compounds of the formula (VI) can be obtained analogously to Example (VI-1) and (VI-2):

TABLE 8

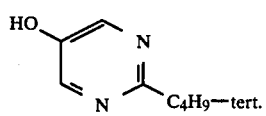

| Example No. | R |
| --- | --- |
| (VI-3) | H |
| (VI-4) | (phenyl) |
| (VI-5) | (cyclopropyl: H$_2$C–CH–CH$_2$) |
| (VI-6) | OCH$_3$ |
| (VI-7) | N(CH$_3$)$_2$ |
| (VI-8) | SCH$_3$ |
| (VI-9) | i-C$_3$H$_7$ |
| (VI-10) | CH$_3$ |

Process for the preparation of the compounds of the general formula (VII) (process stage (d))

EXAMPLE (VII-1)

A solution of 186.5 g (1 mole) of 2-tert.-butyl-4-chloro-5-hydroxy-pyrimidine and 84 g (2.1 moles) of sodium hydroxide in 800 ml of water is hydrogenated at 50° C. under a hydrogen pressure of 10 bar in the presence of 15 g of Raney nickel. After the end of the uptake of hydrogen, the catalyst is filtered off with suction. Concentrated hydrochloric acid is added to the filtrate until the pH reaches 4. The product which has precipitated out is filtered off with suction and rinsed with water.

110 g (77% of theory) of 2-tert.-butyl-5-hydroxypyrimidine are obtained in this manner in the form of a colorless powder with a melting point of 132°C.

EXAMPLE (VII-2)

"One-pot process"

A solution of 2-tert.-butyl-4-chloro-5-methylcarbonyloxy-pyrimidine is prepared by warming a mixture of 105 g (0.5 mole) of 2-tert.-butyl-4-hydroxy-5-methyl-carbonyloxy-pyrimidine, 450 ml of toluene, 1 ml of dimethylformamide and 70 g (0.55 mole) of oxalyl chloride at 60° C. for 6 hours and the solution is added to a mixture of 175 g of 45 per cent strength sodium hydroxide solution and 300 ml of water. The mixture is warmed at 65° C. for 1 hour and the aqueous phase, with the 2-tert.butyl-4-chloro-5-hydroxy-pyrimidine dissolved therein as the sodium salt, is separated off and hydrogenated at 55° C. under a hydrogen pressure of 50 bar in the presence of 75 g of Raney nickel. After separating off the catalyst, the solution is adjusted to pH 4–5 with concentrated hydrochloric acid. The precipitated product is then filtered off with suction, washed with water adn dried at 50° C. in vacuo.

52 g (68% of theory) of 2-tert.-butyl-5-hydroxypyrimidine are obtained in this manner as a beige powder with a melting point of 132° C.

The following compounds of the formula (VII) can be obtained analogously to Example (VII-1) and (VII-2):

TABLE 9

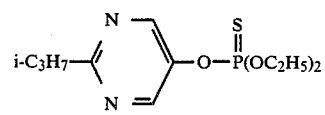 (VII)

| Example No. | R | Melting point [°C.] |
|---|---|---|
| (VII-3) | $C_3H_7-n$ | 117 |
| (VII-4) | H | 216 |
| (VII-5) | $CH_3$ | 173 |
| (VII-6) | $N(CH_3)_2$ | 164 |
| (VII-7) | $C_2H_5$ | 149 |
| (VII-8) | cyclohexyl | 165 |
| (VII-9) | phenyl | 145 |
| (VII-10) | cyclopropyl | |
| (VII-11) | $OCH_3$ | |

TABLE 9-continued

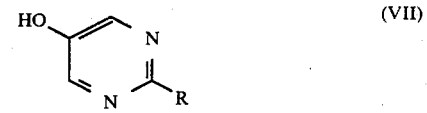 (VII)

| Example No. | R | Melting point [°C.] |
|---|---|---|
| (VII-12) | $SCH_3$ | |

Process for the preparation of the compounds of the general formula (I) (process stage (e))

EXAMPLE (I-1)

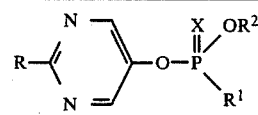

A mixture of 300 ml of acetonitrile, 13.8 g (0.1 mole) of 2-iso-propyl-5-hydroxy-pyrimidine, 20.7 g (0.15 mole) of potassium carbonate and 18.8 g (0.1 mole) of O,O-diethyl-thionophosphoric acid diester chloride is stirred at 45° C. for 2 hours. The reaction mixture is then poured into 400 ml of toluene and washed twice with 300 ml of water each time. The toluene solution is dried over sodium sulphate and evaporated in vacuo. The residue is distilled under a high vacuum.

17.4 g (62% of theory) of O,O-diethyl-O-[2-isopropyl-pyrimidin-5-yl]-thionophosphoric acid ester are thus obtained in the form of a brown oil with the refractive index $n_D^{21}$: 1.4970

The following compounds of the formula (I) can be prepared in an analogous manner:

TABLE 10

(I)

| Example No. | $R^2$ | $R^1$ | R | X | Yield (% of theory) | Refractive index |
|---|---|---|---|---|---|---|
| (I-2) | $C_3H_7-i$ | $CH_3$ | $C_3H_7-i$ | S | 74 | $n_D^{21}$: 1.5102 |
| (I-3) | $CH_3$ | $OCH_3$ | $C_3H_7-i$ | S | 66 | $n_D^{24}$: 1.5080 |
| (I-4) | $C_2H_5$ | $SC_3H_7-n$ | $C_3H_7-i$ | S | 69 | $n_D^{26}$: 1.5284 |
| (I-5) | $C_2H_5$ | phenyl | $C_3H_7-i$ | S | 74 | $n_D^{26}$: 1.5570 |
| (I-6) | $C_2H_5$ | $OC_2H_5$ | $C_3H_7-i$ | O | 82 | $n_D^{32}$: 1.4630 |
| (I-7) | $C_2H_5$ | $NH-C_3H_7-i$ | $C_3H_7-i$ | S | 57 | $n_D^{32}$: 1.5057 |
| (I-8) | $C_3H_7-n$ | $OC_2H_5$ | $C_3H_7-i$ | S | 73 | $n_D^{32}$: 1.4929 |
| (I-9) | $C_2H_5$ | $OC_2H_5$ | $CH_3$ | S | 92 | $n_D^{32}$: 1.4992 |
| (I-10) | $C_2H_5$ | $C_2H_5$ | $CH_3$ | S | 80 | $n_D^{32}$: 1.5169 |
| (I-11) | $C_2H_5$ | $OC_2H_5$ | phenyl | S | 80 | $n_D^{32}$: 1.5643 |
| (I-12) | $C_2H_5$ | $C_2H_5$ | phenyl | S | 80 | $n_D^{32}$: 1.5827 |
| (I-13) | $C_2H_5$ | $OC_2H_5$ | H | S | 72 | $n_D^{32}$: 1.5028 |

TABLE 10-continued $$\text{(I)} \quad R-\overset{N=}{\underset{N=}{\bigvee}}-O-\overset{X}{\underset{R^1}{P}}\overset{OR^2}{}$$

| Example No. | $R^2$ | $R^1$ | R | X | Yield (% of theory) | Refractive index |
|---|---|---|---|---|---|---|
| (I-14) | $C_2H_5$ | $OC_2H_5$ | $C_2H_5$ | S | 84 | $n_D^{20}$: 1.5014 |
| (I-15) | $C_2H_5$ | $OC_2H_5$ | $C_3H_7$—n | S | 60 | $n_D^{26}$: 1.4833 |
| (I-16) | $C_2H_5$ | $OC_2H_5$ | $C_4H_9$—n | S | 94 | $n_D^{21}$: 1.4958 |

EXAMPLE (I-17)

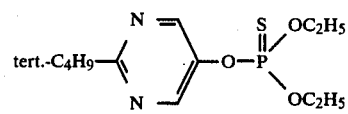

344 g {1.82 moles} of O,O-diethyl-thionophosphoric acid diester chloride are added all at once to a mixture of 277 g (1.82 moles) of 2-tert.-butyl-5-hydroxy-pyrimidine, 306.3 g (2.22 moles) of potassium carbonate, 12.4 g (0.11 mole) of DABCO and 2 l of toluene. The temperature thereby rises up to about 35° C. The mixture is subsequently stirred for 4 hours, without heating, the inorganic salt is filtered off with suction and rinsed with toluene and the filtrate is then evaporated in vacuo. The residue is subjected to incipient distillation at 60° C. under a high vacuum.

516 g (93% of theory) of O,O-diethyl-O-(2-tert.butyl-pyrimidin-5-yl)-thionophosphoric acid ester of refractive index $n_D^{26}$ 1.4902 are thus obtained.

EXAMPLE (I-18)

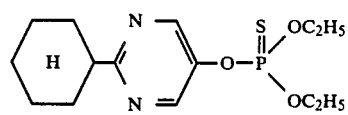

A mixture of 300 ml of acetonitrile, 17.8 g (0.1 mole) of 2-cyclohexyl-5-hydroxy-pyrimidine and 20.7 g (0.15 mole) of O,O-diethylthionophosphoric acid diester chloride is stirred at 45° C. for 2 hours. The reaction mixture is then poured into 400 ml of toluene and washed twice with 300 ml of water each time. The toluene solution is dried over sodium sulphate and evaporated in vacuo. The residue is subjected to incipient distillation under a high vacuum.

21.7 g (66% of theory) of O,O-diethyl-O-(2-cyclohexyl-pyrimidin-5-yl)-thionophosphoric acid ester are thus obtained in the form of a brown oil with a refractive index of $n_D^{23}$: 1.5158.

The following compounds of the formula (I) can be prepared analogously:

TABLE 11

$$\text{(I)} \quad R-\overset{N=}{\underset{N=}{\bigvee}}-O-\overset{X}{\underset{R^1}{P}}\overset{OR^2}{}$$

| Example No. | $R^2$ | $R^1$ | R | X | Yield (% of theory) | Physical data (Refractive index; melting point °C.) |
|---|---|---|---|---|---|---|
| (I-19) | $C_2H_5$ | $NH-C_3H_7$—i | –⟨C₆H₁₁⟩ | S | 51 | $n_D^{23}$: 1.5246 |
| (I-20) | $CH_3$ | $OCH_3$ | –⟨C₆H₁₁⟩ | S | 64 | $n_D^{23}$: 1.5287 |
| (I-21) | $C_2H_5$ | $OC_2H_5$ | –HC(CH₂)₂ (cyclopropyl) | S | 78 | $n_D^{24}$: 1.5142 |
| (I-22) | $C_2H_5$ | $NH-C_3H_7$—i | –HC(CH₂)₂ (cyclopropyl) | S | 62 | 49 |

TABLE 11-continued
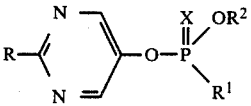
(I)
| Example No. | R² | R¹ | R | X | Yield (% of theory) | Physical data (Refractive index; melting point °C.) |
|---|---|---|---|---|---|---|
| (I-23) | $CH_3$ | $OCH_3$ | 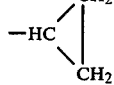 | S | 43 | $n_D^{24}$: 1.5390 |
| (I-24) | $C_3H_7$—n | $OC_2H_5$ | 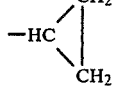 | S | 71 | $n_D^{25}$: 1.5128 |
| (I-25) | $C_2H_5$ | $NH$—$C_2H_5$ |  | S | 74 | $n_D^{26}$: 1.5310 |
| (I-26) | $C_2H_5$ | $OC_2H_5$ | 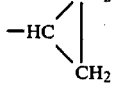 | | | |
| (I-27) | $C_2H_5$ | $OC_2H_5$ | 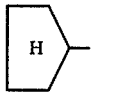 | S | | |
| (I-28) | $C_2H_5$ | $OC_2H_5$ | 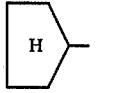 | S | 80 | $n_D^{23}$: 1.5164 |
| (I-29) | $C_2H_5$ | $OC_3H_7$—n | 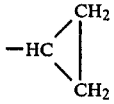 | S | | |
| (I-30) | $C_2H_5$ | $CH_3$ | 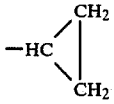 | S | 72 | $n_D^{25}$: 1.5428 |
| (I-31) | $C_2H_5$ | $OC_2H_5$ | 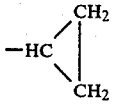 | O | | |
| (I-32) | $C_2H_5$ | $NH$—$C_3H_7$—i |  | O | | |
| (I-33) | $C_2H_5$ | 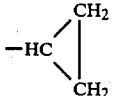 | —HC(CH₂)₂ (cyclopropyl) | S | 74 | $n_D^{25}$: 1.5815 |
| (I-34) | $C_2H_5$ | $SC_3H_7$—n | —HC(CH₂)₂ (cyclopropyl) | S | | |

TABLE 11-continued $$\underset{R}{\overset{N=\!\!=\!\!}{\underset{N=\!\!=\!\!}{\bigvee}}}\!\!\!-\!\!O\!-\!\overset{X}{\underset{R^1}{\overset{\|}{P}}}\!\!\!\overset{OR^2}{\underset{R^1}{\diagdown}}$$ (I)

| Example No. | $R^2$ | $R^1$ | R | X | Yield (% of theory) | Physical data (Refractive index; melting point °C.) |
|---|---|---|---|---|---|---|
| (I-35) | $C_2H_5$ | phenyl | H | S | | |
| (I-36) | $C_2H_5$ | $NH-C_2H_5$ | H | S | 66 | $n_D^{23}$: 1.5329 |
| (I-37) | $C_2H_5$ | $SC_3H_7$ | cyclopropyl | O | | |
| (I-38) | $C_2H_5$ | $C_2H_5$ | cyclopropyl | S | | |
| (I-39) | $CH_3$ | $C_2H_5$ | cyclopropyl | S | | |
| (I-40) | $C_3H_7-i$ | $CH_3$ | cyclopropyl | S | 67 | $n_D^{26}$: 1.5233 |
| (I-41) | $CH_3$ | $NH-C_3H_7-i$ | cyclopropyl | S | | |
| (I-42) | $CH_3$ | $NH-CH_3$ | cyclopropyl | S | 66 | $n_D^{26}$: 1.5460 |
| (I-43) | $C_2H_5$ | $NH-CH_3$ | cyclopropyl | S | | |
| (I-44) | $CH_3$ | $NH-C_2H_5$ | cyclopropyl | S | | |
| (I-45) | $C_2H_5$ | $NH-C_3H_7-i$ | cyclopentyl | S | 55 | $n_D^{23}$: 1.5247 |
| (I-46) | $C_2H_5$ | $OC_2H_5$ | 1-methylcyclopropyl | S | | |

EXAMPLE (I-47)

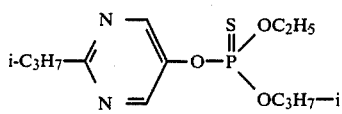

A mixture of 300 ml of acetonitrile, 13.8 g (0.1 mole) of 5-hydroxy-2-iso-propyl-pyrimidine, 20.7 g (0.15 mole) of potassium carbonate and 20.2 g (0.1 mole) of O-ethyl-O-iso-propyl-thiono-phosphoric acid diester chloride is stirred at 45° C. for 2 hours. The reaction mixture is then poured into 400 ml of toluene and is washed twice with 300 ml of water each time. The toluene solution is dried over sodium sulphate and evaporated in vacuo. The residue is subjected to incipient distillation under a high vacuum.

28 g (92% of theory) of O-ethyl-O-isopropyl-O-(2-iso-propyl-pyrimidin-5-yl)-thionophosphoric acid ester are thus obtained in the form of a yellow oil with the refractive index $n_D^{23}$: 1.4910.

The following compounds of the formula (I) can be prepared in an analogous manner:

TABLE 12

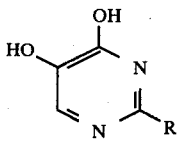
(I)

| Example No. | R | $R^2$ | $R^1$ | Refractive index |
|---|---|---|---|---|
| (I-48) | $C_3H_7$—i | $C_3H_7$—i | $OC_3H_7$—i | $n_D^{20}$: 1.4869 |
| (I-49) | $C_4H_9$—t | $C_2H_5$ | $OC_3H_7$—i | $n_D^{20}$: 1.4917 |
| (I-50) | $C_3H_7$—i | $C_2H_5$ | $OC_4H_9$—s | $n_D^{20}$: 1.4960 |
| (I-51) | $C_4H_9$—t | $C_2H_5$ | $OC_4H_9$—s | $n_D^{22}$: 1.4935 |
| (I-52) | $C_4H_9$—t | $C_3H_7$—i | $OC_3H_7$—i | $n_D^{22}$: 1.4857 |
| (I-53) | phenyl | $C_2H_5$ | $OC_3H_7$—i | $n_D^{22}$: 1.5516 |
| (I-54) | $C_4H_9$—t | $C_2H_5$ | $NHC_2H_5$ | $n_D^{21}$: 1.5100 |
| (I-55) | phenyl | $C_2H_5$ | $OC_4H_9$—s | |
| (I-56) | phenyl | $C_3H_7$—i | $OC_3H_7$—i | |
| (I-57) | $C_3H_7$—i | $C_3H_7$—n | $OC_3H_7$—n | $n_D^{23}$: 1.4915 |

It will be understood that the specification and examples are illustrative but not limitative of the present invention and that other embodiments within the spirit and scope of the invention will suggest themselves to those skilled in the art.

What is claimed is:

1. A process for the preparation of a compound of the formula

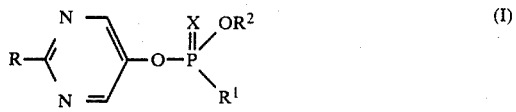

in which

R represents hydrogen, alkoxy with 1 to 12 carbon atoms, alkylamino or dialkylamio with 1 to 5 carbon atoms per alkyl radical; or represents alkyl with 1 to 20 carbon atoms, cycloalkyl with 3 to 8 carbon atoms or aryl with 6 to 10 carbon atoms, each optionally substituted by alkoxy or alkylsulphonyl with 1 to 4 carbon atoms; or represents cycloalkyl with 3 to 8 carbon atoms or aryl with 6 to 10 carbon atoms substituted by alkyl with 1 to 4 carbon atoms, $R^1$ represents optionally substituted alkyl, alkylamino or dialkylamino with 1 to 5 carbon atoms per alkyl radical, optionally alkoxy or alkylthio with 1 to 6 carbon atoms, or phenyl, $R^2$ represents optionally substituted alkyl with 1 to 5 carbon atoms, the optional substituents for $R^1$ and $R^2$ comprising alkyl with 1 to 4 carbon atoms (except for $R^2$ or when $R^1$ is itself alkyl, alkoxy or alkylthio with 1 to 4 carbon atoms, halogen, cyano or nitro, and X represents oxygen or sulphur, comprising
(a) reacting a compound of the formula

with an acylating agent of the formula $$R^3-CO-Y \qquad (III)$$

in which
$R^3$ represents alkyl, alkoxy or aryl and
Y represents halogen or a grouping -OCOR$^3$, at a temperature between 0° C. to give a compound of the formula

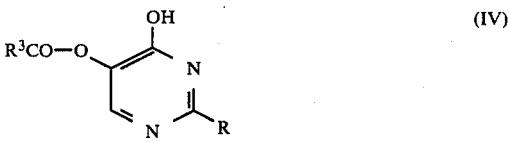

(b) reacting the compound of the formula (IV) with a halogenating agent at a temperature between 10° C. and 120° C. to give a compound of the formula

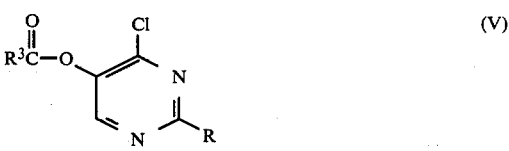

(c) reacting the compound of the formula (V) in the presence of an inorganic base at a temperature between 0° C. and 160° C. to give a salt of the compound of the formula

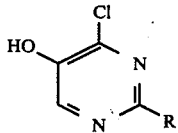

with the base used, (d) reacting the compound of formula (VI) or its salt with hydrogen in the presence of a hydrogenation catlayst at a temperature between 20° C. and 150° C. to give a compound of the formula

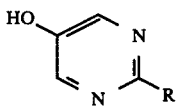

or its salt with the base used in step c), and (e) reacting the compound of formula (VII) or its salt with a compound of the formula

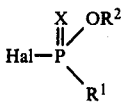

in which Hal represents halogen, to produce the compound of formula (I).

2. A compound of the formula

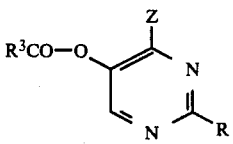

in which
R is i-$C_3H_7$ or tert.-$C_4H_9$, and
$R^3$ is $C_1$-$C_4$-alkyl, and
Z is OH or Cl.

3. A compound according to claim 2, in which
R is tert.-$C_4H_9$, and
$R^3$ is methyl.

4. A process for the preparation of a 4-chloro-5-hydroxy-pyrimidine of the formula

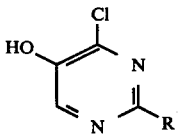

in which R represents hydrogen, alkoxy with 1 to 12 carbon atoms, alkylamino or dialkylamino with 1 to 5 carbon atoms per alkyl radical; or represents alkyl with 1 to 20 carbon atoms, cycloalkyl with 3 to 8 carbon atoms or aryl with 6 to 10 carbon atoms, each optionally substituted by alkoxy or alkylsulphonyl with 1 to 4 carbon atoms; or represents cycloalkyl with 3 to 8 carbon atoms or aryl with 6 to 10 carbon atoms substituted by alkyl with 1 to 4 carbon atoms, or a salt thereof with an inorganic base comprising hydrolyzing a 4-chloropyrimidine derivative of the formula

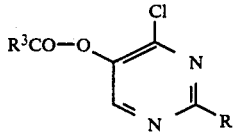

in which $R^3$ is alkyl or alkoxy with 1 to 4 carbon atoms, or aryl with 6 to 10 carbon atoms, in the presence of an inorganic base at a temperature between 0° C. and 160° C.

5. A process according to claim 1, wherein process steps (b), (c) and (d) are carried out without isolation of the intermediate products.

6. A process for the preparation of a compound of the formula

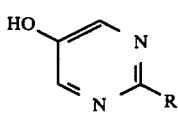

in which R represents hydrogen, alkoxy with 1 to 12 carbon atoms, alkylamino or dialkylamino with 1 to 5 carbon atoms per alkyl radical; or represents alkyl with 1 to 20 carbon atoms, cycloalkyl with 3 to 8 carbon atoms or aryl with 6 to 10 carbon atoms, each optionally substituted by alkoxy or alkylsulphonyl with 1 to 4 carbon atoms; or represents cycloalkyl with 3 to 8 carbon atoms or aryl with 6 to 10 carbon atoms substituted by alkyl with 1 to 4 carbon atoms, comprising reacting a compound of the formula

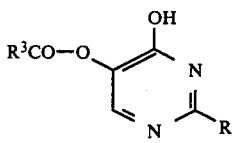

in which $R^3$ is alkyl or alkoxy with 1 to 4 carbon atoms, or aryl with 6 to 10 carbon atoms, with a halogenating agent at a temperature between 10° C. and 120° C., to give a compound of the formula

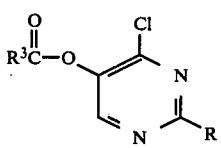

reacting the compound of formula (V) with an inorganic base at a temperature between 0° C. and 160° C. to give a salt of a compound of the formula

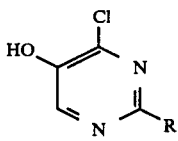

and reacting the salt of the compound of formula (VI) with hydrogen in the presence of a hydrogenation catalyst at a temperature between 20° C. and 150° C., to give a salt of the compound of the formula

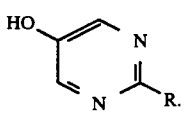

* * * * *

UNITED STATES PATENT AND TRADEMARK OFFICE
CERTIFICATE OF CORRECTION

PATENT NO. : 4,769,458
DATED : September 6, 1988
INVENTOR(S) : Hermann Arold, et al It is certified that error appears in the above-identified patent and that said Letters Patent is hereby corrected as shown below:

| | |
|---|---|
| Col. 4, line 42 | Correct --methylthio-- |
| Col. 6, line 63 | Delete "brqmide" and substitute --bromide-- |
| Col. 9, line 66 | Correct --compound-- |
| Col. 14, line 39 | Middle of formula delete "O" (with ∥ -P) and substitute --S-- (with ∥ -P) |
| Col. 14, line 42 | Delete "proce$s" and substitute --process-- |
| Col. 16, line 29 | Delete "spoil" and substitute --soil-- |
| Col. 16, line 62 | Delete "foC" and substitute --for-- |
| Col. 17, line 26 | Delete "20tert.-" and substitute --2-tert.-- |
| Col. 18, line 15 | Delete "0/05" and substitute --0.05-- |
| Col. 18, line 15 | After "tert." insert -- - -- |
| Col. 18, line 31 | Correct --analogously-- |
| Col. 19, line 15 | Delete "-bytyl-" and substitute -- -butyl- -- |
| Col. 19, line 16 | After "5" insert -- - -- |
| Col. 20, line 68 | Delete "adn" and substitute --and-- |
| Col. 23, line 23 | Before "1.82" delete " { " and substitute --(-- |
| Col. 25, Table II, 4th line under "X" | Insert --S-- |

UNITED STATES PATENT AND TRADEMARK OFFICE
CERTIFICATE OF CORRECTION

PATENT NO. : 4,769,458
DATED : September 6, 1988
INVENTOR(S) : Hermann Arold, et al It is certified that error appears in the above-identified patent and that said Letters Patent is hereby corrected as shown below:

| | |
|---|---|
| Col. 30, line 10 | Correct --dialkylamino-- |
| Col. 30, line 26 | After "alkyl" insert --)-- |
| Col. 30, line 46 | After "0°C." insert --and 160°C-- |
| Col. 31, line 14 | Correct --catalyst-- |
| Col. 32, line 43 | After "(V)" insert --,-- |
| Col. 32, line 53 | After "(VI)" insert --,-- |

Signed and Sealed this

Twenty-eighth Day of March, 1989

Attest:

DONALD J. QUIGG

*Attesting Officer*   Commissioner of Patents and Trademarks